United States Patent [19]
Lavielle et al.

[11] Patent Number: 4,943,577
[45] Date of Patent: Jul. 24, 1990

[54] PIPERAZINYLALKYLPIPERAZINEDIONE COMPOUNDS

[75] Inventors: Gilbert Lavielle, La Celle St-Cloud; Jean C. Poignant, Bures S/Yvette, both of France

[73] Assignee: Adir Et Cie, Neuilly-sur-Seine, France

[21] Appl. No.: 382,252

[22] Filed: Jul. 19, 1989

Related U.S. Application Data

[62] Division of Ser. No. 206,512, Jun. 14, 1988, Pat. No. 4,877,788.

[30] Foreign Application Priority Data

Jun. 15, 1987 [FR] France ................... 87 08263

[51] Int. Cl.$^5$ ............... C07D 471/22; A61K 31/495; A61K 31/505
[52] U.S. Cl. .................... 514/250; 514/252; 514/254; 544/295; 544/343; 544/344; 544/357; 544/408; 546/147
[58] Field of Search ............... 544/295, 343; 514/250

[56] References Cited
U.S. PATENT DOCUMENTS 3,917,599 11/1975 Saxena et al. ............... 544/343
4,021,558 5/1977 Kutter et al. ............... 514/309
4,273,773 6/1981 Demerson et al. ............... 544/343
4,423,232 12/1983 Demerson et al. ............... 548/472
4,877,788 10/1989 Laxielle et al. ............... 514/252

*Primary Examiner*—Mukund J. Shah
*Assistant Examiner*—Emily Bernhaudt
*Attorney, Agent, or Firm*—Gordon W. Hueschen

[57] ABSTRACT

The invention relates to compounds of formula I

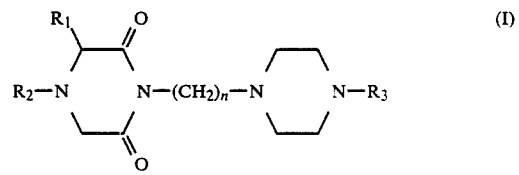

in which
$R_1$ and $R_2$ form together and with the piperazine-2,6-dione radical to which they are attached a hexahydropyrazino-$\beta$-cabbolinedione radical,
$R_3$ denotes a pyrimidinyl radical or a phenyl radical optionally substituted by an alkyl radical of 1 to 4 carbon atoms or a trifluoromethyl radical,
n is an integer of 2 to 4, inclusive.

5 Claims, No Drawings

PIPERAZINYLALKYLPIPERAZINEDIONE COMPOUNDS

This is a division of application Ser. No. 206,512 filed June 14, 1988 now U.P. Pat. No. 4,877,788, issued Oct. 31, 1989. The present invention relates to nitrogenous polycyclic compounds derived from piperazinylalkylpiperazine-2,6-dione, the processes for their preparation and the pharmaceutical compositions containing them.

Certain piperazinedione compounds which have sedative effects on the central nervous system are known. (D. De Jong et coll. J.Pharm., (1959), 11, p.393-399).

The new piperazinedione compounds have highly advantageous pharmacological properties and especially very powerful anxiolytic, antiaggressive and antipsychotic properties. On the other hand, they are devoid of the secondary effects traditionally encountered in this pharmacological class and more especially of anticonvulsivant effects. They are therefore distinguished by this fact from other piperazinedione compounds which are already known. Furthermore, the compounds of the invention are clearly differentiated by their chemical structure from other piperazines and from their derivatives which have already been described.

The subject of the present invention is more particularly the piperazinylalkylpiperazinedione compounds of general formula I,

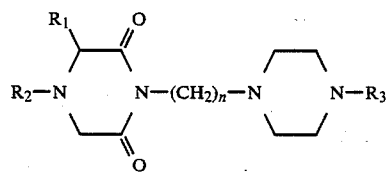

in which,
either
$R_1$ denotes a hydrogen atom, and
$R_2$ denotes a benzyl radical optionally substituted on the benzene ring by a halogen atom or by an alkoxyl radical containing from 1 to 4 carbon atoms,
or
$R_1$ and $R_2$ form together and with the piperazine- 2,6-dione radical to which they are attached a hexahydropyrazinoisoquinolinedione radical or a hexahydropyrazino-$\beta$-carbolinedione radical,
$R_3$ denotes a quinolyl radical, optionally substituted by a phenyl radical or by a nitro radical, an indolyl radical substituted on the nitrogen atom by an acyl radical containing from 1 to 5 carbon atoms, or, provided however that R1 does not simultaneously denote a hydrogen atom, a pyrimidinyl radical or a phenyl radical optionally substituted by an alkyl radical of 1 to 4 carbon atoms or a trifluoromethyl radical,
n is an integer capable of assuming the values from 2 to 4,
and their salts of addition to a pharmaceutically acceptable inorganic or organic acid.

Another subject of the present invention is the process for the preparation of a compound of general formula I, in which:
an imide of general formula II:

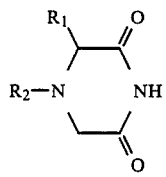

in which $R_1$ and $R_2$ have the meaning defined earlier in the case of formula I, is reacted with a dihalogenated alkyl of general formula III:

$$Br-(CH_2)_n-Cl \quad (III)$$

in which n is an integer capable of assuming values from 2 to 4, in the presence of an alkali metal hydride, to obtain the compound of general formula IV:

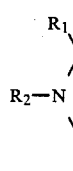

in which $R_1$, $R_2$ and n have the meaning defined above, which is then condensed
either with a piperazine of general formula V:

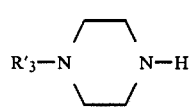

in Which $R_3$ denotes a pyrimidinyl radical, a phenyl radical optionally substituted by an alkyl radical of 1 to 4 carbon atoms or a trifluoromethyl radical, or a quinolyl radical optionally substituted by a phenyl radical or by a nitro group,
in order to obtain a compound of general formula I in which $R_3$ has the same meaning as $R'_3$
or with 4-benzyloxycarbonylpiperazine of general formula VI:

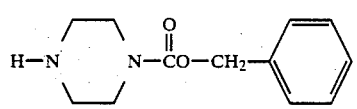

to obtain a compound of general formula VII:

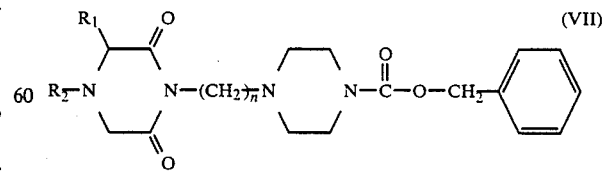

in which $R_1$, $R_2$ and n have the meaning defined above,
which is then subjected to an acidolysis to obtain a piperazine compounds of formula VIII,

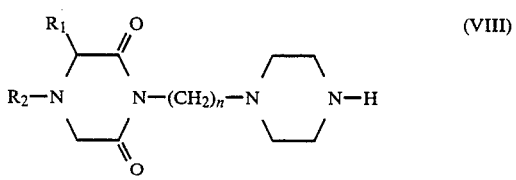

in which the meaning of $R_1$, $R_2$ and n remains identical with that given above, which is condensed with an indole derivative of general formula IX:

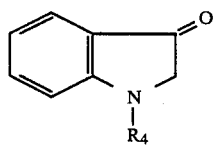

in which $R_4$ denotes an acyl radical containing from 1 to 5 carbon atoms, to form the compounds of general formula I in which $R_3$ denotes an indolyl radical substituted on the nitrogen atom by an acyl radical containing from 1 to 5 carbon atoms, and then, if desired:

the compounds of general formula I are converted into a salt of addition with a pharmaceutically acceptable organic or inorganic acid.

The imides of general formula II are obtained by heating appropriate diacids in the presence of formamide. The latter are prepared by the action of 2-chloroacetic acid on the corresponding primary amines (Organic Syntheses Collective; John Wiley and Sons publ., N.Y., (1943),vol.II, p.397). They may also be synthesized by alkylation of piperazine-2,6-dione with an alkane halide, (Bull.Soc.Chim.France, (1968), 88, p.3248).

The condensation of piperazine-2,6-diones of general formula IV with the piperazines of general formula V is carried out in a polar organic solvent such as 2-butanone in the presence of inorganic salts such as sodium carbonate and sodium iodide at a temperature of between 40° C. and 100° C.

The acidolysis of piperazine-2,6-diones of general formula VII is performed with a 75/25 mixture of acetic acid and hydrobromic acid, at ambient temperature, in an inert organic solvent such as ethyl ether.

The condensation of piperazine-2,6-diones of general formula VIII with the N-acylated indole derivatives of general formula IX is carried out in anhydrous toluene in the presence of an acidic catalyst such as, for example, para-toluenesulfonic acid.

Among the acids which are pharmaceutically acceptable for the preparation of the salts of addition to the compounds of general formula I there may be mentioned phosphoric, hydrochloric, citric, oxalic, sulfuric, tartaric, mandelic and trimethanesulfonic acids, and the like.

The compounds according to the invention and their salts are endowed with highly advantageous pharmacological properties.

In fact, in vivo pharmacological tests have shown that these compounds have powerful anxiolytic, antiaggressive and antipsychotic properties. These properties have been demonstrated by means of tests which are traditionally employed on animals, permitting the anxiolytic, antiaggressive or antipsychotic activity of the new compounds in man to be predicted with very good accuracy. (Dallas Treit., Neur.Biob.Rev.,(1985),9,p.203-222).

In return, the compounds of the present invention are devoid of properties of sedation of the central nervous system and are distinguished from other piperazine-2,6-dione derivatives which are already known.

In particular, the compounds of the present invention have an anxioselective psychotropic agent profile. Their pharmacological properties permit them to be applied in the treatment of anxiety in all its forms.

The invention also extends to the pharmaceutical compositions containing, as active principle, at least one compound of general formula I or one of its salts of addition with a pharmaceutically compatible inorganic or organic acid, in combination with one or more inert and suitable excipients.

The pharmaceutical compositions thus obtained are advantageously presented in various forms such as, for example, tablets, coated pills, gelatin capsules, sublingual tablets or other galenic preparations which are suitable for a sublingual administration, suppositories and injectable or drinkable solutions.

The posology can vary widely as a function of the patient's age and weight, on the nature and on the severity of the disorder and on the route of administration.

The preferred administration route is the oral or parenteral route. As a general rule, the unit posology will range between 0.1 and 100 mg and the daily posology which can be employed in human therapeutics between 0.1 and 300 mg.

The following examples, which are given without any limitation being implied, illustrate the invention.

The melting points shown are measured using the micro-Köfler technique. The infrared spectra are obtained with solutions of the products in Nujol. The proton nuclear magnetic resonance spectra (NMR) were recorded at 60 MHz.

EXAMPLE 1

2-{3-[4-(3-trifluoromethylphenyl)-1-piperazinyl]-propyl}-1,3,4,6,11,11a-hexahydro-2H-pyrazino[1,2-b]isoquinoline-1,3-dione dihydrochloride Stage A 3-Carboxy-1,2,3,4-tetrahydro-2-isoquinolylacetic acid At 25° C., add 2.25 moles of sodium hydroxide dissolved in 280 ml of water to a solution of 1.12 moles of sodium 2-chloroacetate in 500 ml of water. Then introduce 1.12 moles of 1,2,3,4-tetrahydro-2-isoquinoleic acid. Heat the reaction mixture to approximately 70° C. until a clear solution is obtained.

At 40° C., add a solution of 1.18 moles of barium chloride in 600 ml of water. Then heat to 90° C. for 15 minutes and then filter quickly. Rinse the precipitate with two 350-ml portions of hot water. Dry and place 0.85 mole of this precipitate in 800 ml of water. Add 0.92 mole of sulfuric acid dissolved in water. Reflux for 10 minutes. Filter off the barium sulfate precipitate. Concentrate the aqueous phase until the diacid has precipitated. Filter. Dry.

Melting point: 218° C.

Yield: 65%

Stage B 1,3,4,6,11,11a-Hexahydro-2H-pyrazino[1,2-b]isoquinoline-1,3-dione

Heat a suspension of 0.46 mole of the diacid obtained previously in 300 ml of formamide for 1 and a half hours at 120° C. and then 5 hours at 160° C. Then cool to 20° C. to obtain crystallization of the imide. Filter. Rinse with ether.

Melting point: 182° C.
Yield: 60%

Stage C 2-(3-Chloropropyl)-1,3,4,6,11,11a-hexahydro-2H-pyrazino[1,2-b]isoquinoline-1,3-dione Add a solution of 0.046 mole of the imide obtained previously in 60 ml of dimethylformamide to a suspension of 0.046 mole of sodium hydride in 100 ml of dimethylformamide. Heat to 60° C. for 45 minutes. Cool to 25° C. and add 0.05 mole of 1-bromo-3-chloropropane. Continue stirring at 25° C. until the imide has disappeared. Evaporate off the solvent under vacuum. Take up the residue with benzene. Wash with water. Dry the organic phase over anhydrous sodium sulfate. Concentrate under vacuum. Crystallize from an ether-acetone mixture.

Melting point : 97° C.
Yield : 72%

Stage D

Reflux for 48 hours a mixture of 0.03 mole of the compound obtained above, 0.03 mole of 4-(3-trifluoromethylphenyl)piperazine, 5 g of sodium carbonate and 0.5 g of sodium iodide in 200 ml of 2-butanone. Cool, filter off the inorganic salts, concentrate under vacuum. Take up the residue with water and extract with benzene. Dry the organic phase over anhydrous sodium sulfate. Evaporate off the solvent under vacuum. Crystallize from a mixture of isopropyl ether and petroleum ether (10:90 v/v). Recrystallize from isopropyl ether.

Dissolve the product obtained in the minimum quantity of acetone. Add two equivalents of hydrochloric ethanol. Filter off the dihydrochloride obtained.

Melting point: 167° C.
Yield: 65%

The spectral physical constants of the base are shown in Table I.

EXAMPLE 2

20
2-{4-[4-(2-Pyrimidyl)-1-piperazinyl]butyl}-1,3,4,6,11,11a-hexahydro-2H-pyrazino[1,2-b]isoquinoline-1,3-dione tartrate

Stage A 2-(4-Chlorobutyl)-1,3,4,6,11,11a-hexahydro-2H-pyrazino-[1,2-b]isoquinoline-1,3-dione This compound was prepared according to the process described in stage C of Example 1 and using 1-bromo-4-chlorobutane instead of 1-bromo-3-chloropropane and heating for one hour at approximately 90° C. To purify the crude compound, chromatograph on a silica column, using dichloromethane as elution solvent and then concentrate the eluate under vacuum.

Yield: 50%

Stage B

2-{4-[4-(2-Pyrimidyl)-1-piperazinyl]butyl}-1,3,4,6,11,11a-hexahydro-2H-pyrazino[1,2-b]isoquinoline-1,3-dione is obtained according to the process described in Example 1, Stage D, and using 4-(2-pyrimidinyl)piperazine instead of 4-(3-trifluoromethylphenyl)piperazine.

It was purified on a silica column using a dichloromethaneethanol mixture as eluent (gradient 99:1 to 95:5 v/v). The spectral physical constants of this base are shown in Table I.

After concentration under vacuum, the residue is dissolved in the minimum quantity of ethanol. Add the required stoichiometric quantity of DL-tartaric acid, dissolved in ethanol. Concentrate under vacuum, crystallize from ethyl ether. Filter.

Melting point: 92° C.
Yield: 60%

EXAMPLE 3

2-{3-[4-(3-Trifluoromethylphenyl)-1-piperazinyl]propyl}-1,3,4,6,12,12a-hexahydro-2H-pyrazino[1,2-b]-8-carboline-1,3-dione dihydrochloride This compound was prepared according to the process described in Example 1. The starting acid employed in stage A is described in J.Med.-Chem.,(1973),16,No.4, p.419.

Yield: 40%
Melting point: 195° C.

The spectral physical constants of 2-{3-[4-(3-trifluoromethylphenyl)-1-piperazinyl]propyl}-1,3,4,6,12,12a-hexahydropyrazino[1,2-b]-8-carboline-1,3-dione are given in Table I.

EXAMPLE 4

2-{4-[4-(2-Pyrimidyl)-1-piperazinyl]butyl}-1,3,4,6,12,12a-hexahydro-2H-pyrazino[1,2-b]-8-carboline-1,3-dione This compound was prepared according to the process described in Example 1, but using the appropriate acid in stage A, 1-bromo-4-chlorobutane in stage C and 4-(2-pyrimidinyl)piperazine in stage D.

The spectral physical constants are shown in Table I.
Melting point: 217° C.
Yield: 45%

EXAMPLE 5

4-(2-Fluorobenzyl)-1-{3-[4-(6-nitro-2-quinolyl)-1-piperazinyl]propyl}piperazine-2,6-dione

Stage A 1-(3-Chloropropyl)-4-(2-fluorobenzyl)piperazine-2,6-dione

Prepare a suspension of 0.12 mole of sodium hydride in 100 ml of dimethylformamide. Add 0.12 mole of 4-(2-fluorobenzyl)piperazine-2,6-dione dissolved in 50 ml of dimethylformamide. Heat to 70° C. for 30 minutes. Cool and add 0.13 mole of 1-bromo-3-chloropropane. Allow to react at ambient temperature until the imide has disappeared completely. Then remove the organic solvent under vacuum and take up the residue with 100 ml of water and 200 ml of benzene.

Allow to separate, remove the aqueous phase and evaporate down the organic phase. The residue is triturated in ether. Pure crystals of 1-(3-chloropropyl)-4-(2-fluorobenzyl)piperazine-2,6-dione are obtained.

Yield: 96%.

Stage B

Add a mixture containing 6 g of sodium carbonate and 0.5 g of sodium iodide to a solution of 0.025 mole of 1-(3-chloropropyl)-4-(2-fluorobenzyl)piperazine-2,6-dione obtained previously and of 0.0275 mole of 4-(6-nitro-2-quinolyl)piperazine (J.Chem.-Soc.,(1949),54,p.227-229 and J.Med.-Chem.,(1985)28,p.1394-98) in 200 ml of 2-butanone. Reflux for 40 hours and then filter and concentrate under vacuum. Take up the residue in benzene and wash the benzene phase three times with distilled water. Dry the organic phase over anhydrous sodium sulfate and evaporate off the solvent. Purify the residue obtained by chromatography on a silica column using a mixture of dichloromethane and methanol (95:5 v/v) as eluent.

Melting point: 153° C.

Yield: 60%

The spectral physical constants of this base are described in Table I.

EXAMPLE 6

4-(2-Fluorobenzyl)-1-{3-[4-(4-phenyl-2-quinolyl)-1piperazinyl]propyl}piperazine-2,6-dione ditartrate This compound was prepared according to the process described in Example 5 but using 4-(4-phenyl-2-quinolyl)piperazine instead of 4-(6-nitro-2-quinolyl)-piperazine in stage B. The preparation of the former compound is known. (J.Am.Chem.-Soc.,(1948),70,p.2402 and J.Med.Chem.,(1985),28,p.13-94-98).

Melting point: =95° C.

Yield: 30%

The spectral physical constants of the base are given in Table I.

EXAMPLE 7

1-{3-[1-(1-Acetyl-3-indolyl)-4-piperazinyl]propyl}-4-(2-methoxybenzyl)piperazine-2,6-dione dihydrochloride

Stage A

1-[3-(1-Benzyloxycarbonyl-4-piperazinyl)propyl]-4-(2-methoxybenzyl)piperazine-2,6-dione This compound was prepared according to the process described in Example 5 by condensing 4-(2-methoxybenzyl)-1-(3-chloropropyl)piperazine-2,6-dione with 4benzyloxycarbonylpiperazine.

Melting point: <50° C.

Yield: 82%

4-Benzyloxycarbonylpiperazine is obtained according to the process described in Synthesis,(1984),12,p.1032.

Stage B

1-[3-(4-Piperazinyl)propyl](2-methoxybenzyl)piperazine-2,6-dione

The amine obtained above (0.08 mole) is dissolved in 200 ml of a mixture of acetic acid and of gaseous hydrobromic acid (75:25 w/w). After 2 hours' stirring at 25° C., dilute with 800 ml of ether. Filter off the precipitate. Rinse with ethyl ether. The precipitate is taken up in water and washed with chloroform. The aqueous phase is then alkalified (pH=10), the amine is extracted with chloroform. The organic phase is dried over sodium sulfate and concentrated under vacuum.

Yield: 70%.

Stage C

Reflux a mixture of 0.027 mole of amine obtained in the previous stage, of 0.023 mole of N-acetyl-3-indolinone (synthesis according to D. Nenitzescu Rev.Roum. Chem.,(1967),12,(2),p.105-8), and of 0.015 mole of para-toluenesulfonic acid in 150 ml of dry toluene. Continue refluxing until the theoretical quantity of water, namely 0.7 ml is obtained. Concentrate under vacuum. Take up the residue in water. Extract with benzene. Dry the organic phase over sodium sulfate. Evaporate down under vacuum. Purify the oil obtained by chromatography on silica (300 g). Elute using an ethyl ether - acetone gradient of 90:10 to 70:30 (v/v). Concentrate the eluent under vacuum. Dissolve the residue in 100 ml of an ethyl ether - ethanol mixture (96:4 v/v). Add two equivalents of hydrochloric ethanol. Filter off the precipitate formed.

Melting point: 183° C.

Yield: 20%

The spectral physical constants of 1-{3-[1-(1-acetyl-3-indolyl)-4-piperazinyl]propyl}-4-(2-methoxybenzyl)-piperazine-2,6-dione are given in Table I.

TABLE 1

COMPOUND OF GENERAL FORMULA I

| EX | Structure (R₁–/R₂–N ring) | n | R₃ | IR cm⁻¹ ν(C=O) | NMR solvent |
|---|---|---|---|---|---|
| 1 | tetrahydroisoquinoline-fused diketopiperazine | 3 | 3-CF₃-phenyl | 1680, 1730 | (CDCl₃) 1.8 ppm, m, 2H; 2.4 to 3.2 ppm, m, 10H; 3 to 4 ppm, m, 9H; 6.8 to 7.5 ppm, m, 8H |
| 2 | tetrahydroisoquinoline-fused diketopiperazine | 4 | 2-pyrimidinyl | 1680, 1730 | (CDCl₃) 1 to 1.8 ppm, m, 4H; 2 to 2.7 ppm, m, 6H; 2.7 to 4 ppm, m, 13H; 6.4 ppm, t, 1H; 7.1 ppm, m, 4H; 8.3 ppm, d, 2H |
| 3 | tetrahydro-β-carboline-fused diketopiperazine | 3 | 3-CF₃-phenyl | 1660, 1730 | (CDCl₃) 2 ppm, m, 2H; 2.3 to 2.9 ppm, m, 6H; 2.9 to 3.5 ppm, m, 6H; 3.5 to 4.2 ppm, m, 7H; 7 to 7.8 ppm, m, 8H; 9.6 ppm 1H exchangeable |
| 4 | tetrahydro-β-carboline-fused diketopiperazine | 4 | 2-pyrimidinyl | 1655, 1740 | (CDCl₃ + DMSO) 1.2 to 1.9 ppm, m, 4H; 2.3 to 2.6 ppm, m, 6H; 2.9 to 3.3 ppm, m, 2H; 3.4 to 3.9 ppm, m, 4H; 3.5 to 4 ppm, m, 5H; 3.7 to 4.2 ppm, m, 2H; 6.5 ppm, m, 1H; 6.6 to 7.6 ppm, m, 4H; 8.25 ppm, d, 2H; 10.6 ppm 1H exchangeable |

TABLE 1-continued
COMPOUND OF GENERAL FORMULA I $$\text{R}_1\text{-ring with } \text{R}_2\text{-N, two C=O, N-(CH}_2)_n\text{-N, piperazine N-R}_3$$

| EX | (R₁, R₂ structure) | n | R₃ | IR cm⁻¹ υ(C=O) | NMR solvent |
|---|---|---|---|---|---|
| 5 | 2-fluorobenzyl on N | 3 | 6-nitroquinolin-2-yl | 1675, 1735 | (CDCl₃) 1.5 to 2.1 ppm,m,2H; 2.2 to 2.7 ppm,m,6H; 3.4 ppm,s,4H; 3.6 to 4.1 ppm,m,8H; 7 to 7.5 ppm,m,5H; 7.7 ppm,d,1H; 8 ppm,d,1H; 8.4 ppm,dd,1H; 8.6 ppm,d,1H |
| 6 | 2-fluorobenzyl on N | 3 | 2-(2-phenyl-phenyl-methylene)pyridyl-type | 1680, 1735 | (CDCl₃) 1.5 to 2.1 ppm,m,2H; 2.2 to 2.8 ppm,m,6H; 3.4 ppm,s,4H; 3.6 to 4 ppm,m,8H; 6.8 to 8 ppm,m,14H |
| 7 | 2-methoxybenzyl on N | 3 | N-acetyl-2-phenyl-vinyl | 1680, 1740 | (CDCl₃) 1.5 to 1.9 ppm,m,2H; 2.2 ppm,s,3H; 2.3 to 2.9 ppm,m,6H; 3.2 ppm,m,4H; 3.4 ppm,s,4H; 3.8 ppm,s,3H; 3.6 to 4 ppm,t,2H and s,2H; 6.7 to 7.6 ppm,m,9H |

PHARMACOLOGICAL STUDY

EXAMPLE 8

Evaluation of the anxiolytic activity by means of the four plates test

The anxiolytic activity of the compounds of general formula I has been investigated in the mouse according to the method of Aron, Simon, Larousse and Boissier, described in Neuropharmacology,(1971),10,p. 459–469. After treating the animals with various doses of the compounds of the invention, administered intraperitoneally or orally, the increase in the percentage of the transitions during the exploration of the bottom of the test-cage, in the presence of electric shocks, has been evaluated. The results of this study are shown in Tables II and III.

TABLE II

| COMPOUND OF EXAMPLE | I.P. DOSE (mg kg$^{-1}$) | % INCREASE IN THE RESPONSES (TRANSITIONS) |
|---|---|---|
| 1 | 10 (S) | 47 |
| 1 | 25 (S) | 57 |
| 2 | 10 (b) | 39 |
| 3 | 50 (b) | 16 |
| 4 | 5 (b) | 22 |

(S) = Salt
(b) = base

TABLE III

| COMPOUND OF EXAMPLE | p.o. DOSE (mg kg$^{-1}$) | % INCREASE IN THE RESPONSES (TRANSITIONS) |
|---|---|---|
| 1 | 5 (b) | 12 |
| 1 | 10 (b) | 33 |

EXAMPLE 9

Inhibition of the isolation aggressiveness in the mouse

The compounds of general formula I inhibit the attack behavior of mice rendered aggressive by isolation according to the method described by Yen, Stanger and Millman in Arch. Int. Pharmacodyn., (1959), 123, p. 179–185. The effect on aggressiveness is evaluated as the percentage of the animals becoming nonaggressive ("protected") after treatment. The results of this test are given in Table IV.

TABLE IV

| COMPOUND OF EXAMPLE | I.P. DOSE (mg kg$^{-1}$) (b) | % OF PAIRS MADE NONAGGRESSIVE |
|---|---|---|
| 1 | 12.5 | 56 (S) |
|   | 25.0 | 89 (S) |
| 2 | 12.5 | 50 (S) |
|   | 25.0 | 100 (S) |
| 3 | 12.5 | 40 (S) |
|   | 25.0 | 90 (S) |
| 4 | 12.5 | 78 (S) |
|   | 25.0 | 88 (S) |

(S) = significant $p < 0.05$
(b) = base

EXAMPLE 10

Inhibition of aggressiveness in the isolated and bulbectomized rat

The compounds of the present invention inhibit the aggressiveness in the isolated and bulbectomized rat. The inhibition in aggressiveness was evaluated according to the method described by Vergnes and Karli in C.R.Soc. Biol.,(1963),157,p.1061. The effect on aggressiveness is evaluated as the percentage of the animals which no longer kill after treatment. The results of this test are indicated in Table V.

TABLE V

| EXAMPLE | I.P. DOSE (salt) (mg kg$^{-1}$) | % OF THE NON-KILLER ANIMALS |
|---|---|---|
| 1 | 25 | 55 |
| 3 | 12.5 | 36 |
| 7 | 12.5 | 25 |

EXAMPLE 11

Inhibition of the conditioned response of active avoidance in the rat

The results obtained with the compounds of general formula I in the course of various experiments employing the method described by Courvoisier et coll. in Arch.Int.Pharmacodyn.,(1953),92,p.305–361 and by Janssen et coll. in Arzneim.Forsch,(1965),15, p. 104–117 are reported in Table VI. The percentages of inhibition of the conditioned avoidance response which were obtained (% ICAR) show that the compounds of the invention have an advantageous antipsychotic property.

TABLE VII

| EXAMPLE | I.P. DOSE (mg kg$^{-1}$) | % I.C.A.R. |
|---|---|---|
| 1 | 20 | 11 |
| 2 | 20 | 32 |
| 3 | 20 | 25 |

EXAMPLE 12

Evaluation of the anxiolytic activity using the MacMillan conflict test

In these conditioning experiments operating in the presence of a feed reward and carried out on the rat, according to the method described by MacMillan in Fed. Proceedings,(1975),34,(9),p.1870–1879, two parameters in the behavioral responses of the animal are considered. The first parameter is the variation in the proportion of punished responses, in the presence of an electric shock, under the influence of the treatment compared with the proportion of punished responses under the influence of physiological serum. The second parameter is the variation in the proportion of unpunished responses, without electric shock, under the influence of the same treatment, compared with the proportion of unpunished responses, when physiological serum is administered. A specific anxiolytic effect is found when after the administration of a substance the proportion of the punished responses alone is found to have increased. As the results shown in Table VII demonstrate, the compound of Example 1 gives positive results when administered intraperitoneally in a dose of 10 mg kg$^{-1}$.

TABLE VII

| EXAMPLE | % VARIATION IN THE PUNISHED RESPONSES | % VARIATION IN THE UNPUNISHED RESPONSES |
| --- | --- | --- |
| 1 | +49 S | +10 NS |

S = significant p < 0.016

EXAMPLE 13

Investigation of secondary effects

The anticonvulsive effect of the compounds of the invention has been evaluated in the mouse by investigating an antagonism towards the convulsions induced by a pentylenetetrazole dose of 100 mg kg$^{-1}$ administered intraperitoneally.

The compounds of general formula I, administered intraperitoneally in a dose of 50 mg kg-1 do not protect the animals against convulsions. At this dosage, therefore, they did not have any considerable anticonvulsivant component.

PHARMACEUTICAL PREPARATION

EXAMPLE 14

Tablets containing a 2 mg dose of 2-{3-[4-(3-trifluoromethylphenyl)-1-piperazinyl]-propyl}-1,2,3,4,11,11a-hexahydro-2H-pyrazino[1,2-b]isoquinoline-1,3-dione 2-{3-[4-(3-Trifluoromethylphenyl)-1-piperazinyl]-propyl}-1,2,3,4,11,11a-hexahydro-2H-pyrazino[1,2-b]isoquinoline-1,3-dione 2 g
Wheat starch 100 g
Corn starch 20 g
Magnesium stearate 15 g
Talc 20 g
for 1,000 tablets each containing 2 mg of active principle.

We claim:

1. A compound selected from those of formula I:

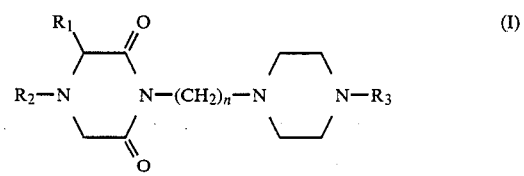

in which
R$_1$ and R$_2$ form together and with the piperazine-2,6-dione radical to which they are attached a hexahydropyrazino-$\beta$-carbolinedione radical,
R$_3$ denotes pyrimidinyl radical or a phenyl radical optionally substituted by an alkyl radical of 1 to 4 carbon atoms or a trifluoromethyl radical,
n is an integer of 2 to 4, inclusive, and addition salts thereof with a pharmaceutically acceptable inorganic or organic acid.

2. Compound of claim 1 being 2-(3-[4-(3-Trifluoromethylphenyl)-1-piperazinyl]-propyl}-1,3,4,6,12,12a-hexahydro-2H-pyrazino[1,2-b]-$\beta$ carboline-1,3-dione and its addition salts with a pharmacuetically acceptable inorganic or organic acid.

3. Pharmaceutical composition useful as an anxiolytic, antiaggressive, or antipsychotic medication, containing, as active principle, a compound as claimed in claim 1 in combination or as a mixture with an excipient or a nontoxic inert carrier which is pharmaceutically acceptable.

4. Oral pharmaceutical composition as claimed in claim 3 containing the active principle in the dosage of 0.1 to 100 mg.

5. A method of treating a disorder requiring anxiolytic, antiaggressive, or antipsychotic medication for the alleviation thereof comprising the step of administering to a subject suffering from such disorder an effective anxiolytic, antiaggressive, or antipsychotic amount of a compound of claim 1.

* * * * *

United States Patent and Trademark Office
CERTIFICATE OF CORRECTION

PATENT NO. : 4,943,577

DATED : July 24, 1990

INVENTOR(S) : Gilbert Lavielle, Jean C. Poignant

It is certified that error appears in the above-identified patent and that said Letters Patent is hereby corrected as shown below:

Title Page, [56] References Cited, U. S. PATENT DOCUMENTS, last reference; "Laxielle" should read -- Lavielle --.

Title Page, Assistant Examiner -; "Bernhaudt" should read -- Bernhardt --.

Title Page, [57] ABSTRACT, line 5 from bottom; "-cabbolinedione" should read -- -carbolinedione --.

Column 6, approximate line 24; "-8-" should read -- β --.

Column 6, approximate line 34; "-8-" should read -- β --.

Column 6, approximate line 38; "-8-" should read -- β --.

Column 7, approximate line 38; "1piperazinyl]" should read -- 1-piperazinyl] --.

Column 8, line 12; "4benzyloxycarbonylpiperazine." should read -- 4-benzyloxycarbonylpiperazine. --.

Column 13, approximate line 36, after "Table III", before "EXAMPLE 9" insert -- (b) = base --.

Column 15, approximate line 18; "kg-1" should read -- $kg^{-1}$ --.

Signed and Sealed this

Nineteenth Day of November, 1991

Attest:

HARRY F. MANBECK, JR.

Attesting Officer

Commissioner of Patents and Trademarks